United States Patent
Sahib et al.

(10) Patent No.: US 9,707,275 B2
(45) Date of Patent: Jul. 18, 2017

(54) STABLE AQUEOUS COMPOSITION COMPRISING HUMAN INSULIN OR AN ANALOGUE OR DERIVATIVE THEREOF

(71) Applicant: WOCKHARDT LIMITED, Aurangabad (IN)

(72) Inventors: Maharaj K Sahib, Aurangabad (IN); Jeetendra Kashinath Ambulge, Aurangabad (IN); Gauravkumar Ramanlal Agrawal, Jalgaon (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 14/436,888

(22) PCT Filed: May 24, 2013

(86) PCT No.: PCT/IB2013/054286
§ 371 (c)(1),
(2) Date: Apr. 18, 2015

(87) PCT Pub. No.: WO2014/096985
PCT Pub. Date: Jun. 26, 2014

(65) Prior Publication Data
US 2015/0265683 A1   Sep. 24, 2015

(30) Foreign Application Priority Data
Dec. 19, 2012 (IN) .................. 3563/MUM/2012

(51) Int. Cl.
| | | |
|---|---|---|
| *A61K 38/28* | (2006.01) | |
| *A61K 47/22* | (2006.01) | |
| *A61K 47/34* | (2017.01) | |
| *A61K 9/00* | (2006.01) | |
| *A61K 9/08* | (2006.01) | |
| *A61K 47/18* | (2017.01) | |
| *A61K 47/10* | (2017.01) | |

(52) U.S. Cl.
CPC ............ *A61K 38/28* (2013.01); *A61K 9/0019* (2013.01); *A61K 9/08* (2013.01); *A61K 47/183* (2013.01); *A61K 47/22* (2013.01); *A61K 47/34* (2013.01); *A61K 47/10* (2013.01); *A61K 47/18* (2013.01)

(58) Field of Classification Search
CPC .............................. A61K 38/28; A61K 47/183
USPC ........................................................ 514/5.9
See application file for complete search history.

(56) References Cited

U.S. PATENT DOCUMENTS

| | | | | |
|---|---|---|---|---|
| 4,371,523 A | * | 2/1983 | Grodsky | A61K 47/183 514/6.7 |
| 5,656,722 A | * | 8/1997 | Dorschug | C07K 14/62 530/303 |
| 7,476,652 B2 | * | 1/2009 | Brunner-Schwarz | A61K 9/0019 514/1.1 |
| 7,713,930 B2 | * | 5/2010 | Brunner-Schwarz | A61K 9/0019 514/1.1 |
| 2008/0039365 A1 | * | 2/2008 | Steiner | A61K 31/185 514/5.9 |

* cited by examiner

*Primary Examiner* — David Lukton
(74) *Attorney, Agent, or Firm* — Bio Intellectual Property Services, LLC, (Bio IPS); O. (Sam) Zaghmout

(57) ABSTRACT

A stable aqueous insulin preparation comprising human insulin, analogs or derivatives thereof, one or more solubility enhancing agents are selected from urea, amino acids and/or surfactants optionally one or more other pharmaceutically acceptable excipient(s).

15 Claims, No Drawings

STABLE AQUEOUS COMPOSITION COMPRISING HUMAN INSULIN OR AN ANALOGUE OR DERIVATIVE THEREOF

FIELD OF THE INVENTION

The present invention provides a pharmaceutical composition comprising human insulin analogue or derivatives thereof, a solubilizer, and optionally one or more other pharmaceutically acceptable excipient(s). The invention relates to parenteral preparations comprising the said formulations. The present invention also provides methods for preparing the said pharmaceutical composition, for improving the stability of insulin preparations and their use for the treatment of diabetes.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Insulin injections are prescribed to the patients suffering from diabetes. Insulin is a natural hormone, which controls the level of the sugar glucose in the blood. In healthy people, insulin is released in blood by the pancreas as the concentration of blood glucose rises. Increased blood glucose levels, occur after meals and are rapidly compensated by a corresponding increase in insulin secretion. Insulin plays major role in converting the excess blood glucose into glycogen and storing it in liver.

Since the introduction of insulin in the 1920's, continuous strides have been made to improve the treatment of diabetes mellitus. To help avoid extreme glycaemia levels, diabetic patients often practice multiple injection therapy, whereby insulin is administered with each meal.

Insulin is a polypeptide of 51 amino acids, which are divided into 2 amino acid chains: the A chain having 21 amino acids and the B chain having 30 amino acids. The chains are connected to one another by means of two disulfide bridges. Insulin preparations have been employed for diabetes therapy for many years.

Traditionally short acting regular Insulin formulations or its intermediate acting Insulin Protamine formulations were used for treating patients with diabetes mellitus. With time, new insulin analogues and derivatives were developed. Insulin analogues and derivatives differ from human insulin at one or more than one amino acid positions and/or amino acid chain length.

A number of insulin, insulin analogs and derivatives are available in the market. The commonly used types of insulin, insulin analogs or insulin derivatives are categorized as:

Rapid-Acting Insulin Analogs:
For example insulin aspart (Novolog®) or insulin lispro (Humalog®). These analogs begin to work within 5 to 15 minutes of administration and are active for 3 to 4 hours.

Short-Acting Insulin:
For example Regular insulin (Humulin® or Novolin®). Regular insulin starts working within 30 minutes after administration and duration of action lasts from about 5 to 8 hours.

Intermediate-Acting Insulin: For Example as Isophane Insulin. It Starts Working in 1 to 3 hours after administration. Its duration of action varies between 16 to 24 hours.

Long-Acting Insulin:
For example Insulin glargine and Insulin detemir. Both these analogs starts working within 1 to 2 hours and their duration of action varies from about 12 to about 24 hours.

Mixed Insulins:
For example mixture of NPH and regular insulin. There are several variations with different proportions of the mixed insulins. The onset of action of these mixed preparations is about 30 minutes.

Ideally, exogenous insulin is administered at times and in doses that would yield a plasma profile, which mimics the plasma profile of endogenous insulin in a normal individual. Insulin preparations containing analogs of human insulin have shown an absorption profile very close to the normal plasma profile.

The insulin preparations of naturally occurring insulin on the market for insulin substitution differ in the origin of the insulin (e.g. bovine, porcine, human insulin, or another mammalian or animal insulin), and also the composition, whereby the profile of action (onset of action and duration of action) can be influenced. By combination of various insulin preparations, very different profiles of action can be obtained. Preparations of naturally occurring insulins, as well as preparations of insulin derivatives or insulin analogs which show modified kinetics, have been on the market for some time. Recombinant DNA technology today makes possible the preparation of such modified insulins.

These include insulin glargine Gly(A21)-Arg(B31)-Arg(B32)-human insulin with a prolonged duration of action. Insulin glargine is injected as an acidic, clear solution and precipitates on account of its solution properties in the physiological pH range of the subcutaneous tissue as a stable hexamer associate. Insulin glargine is injected once daily and is distinguished compared with other long-acting insulins by its flat serum profile and the reduction of the danger of nightly hypoglycemia associated therewith (Schubert-Zsilavecz et al., 2: 125-130(2001)).

Fast acting insulin(s) are used to control post-prandial increase in the sugar levels. The fast acting insulins include Insulin Lispro, Insulin aspart and Insulin Glulisine. Insulin aspart, $Asp^{B28}$ human insulin, is a fast-acting medication that begins to work very quickly. It is used to treat type 1 (insulin-dependent) diabetes and type 2 (non-insulin-dependent) diabetes. Insulin aspart is usually given together with another long-acting insulin.

Insulin analogs having an accelerated onset of action are described in EP0214826, EP0375437 and EP0678522. EP0124826 relates, inter alia, to substitutions of B27 and B28. EP0678522 describes insulin analogs, which have various amino acids, preferably proline, in position B29, but not glutamic acid.

EP0375437 includes insulin analogs with lysine or arginine in B28, which can optionally additionally be modified in B3 and/or A21. In EP0419504, insulin analogs are disclosed which are protected against chemical modifications, in which asparagine in B3 and at least one further amino acid in the positions A5, A15, A18 or A21 are modified. In WO 92/00321, insulin analogs are described in which at least one amino acid of the positions B1-B6 is replaced by lysine or arginine. According to WO92/00321, insulins of this type have a prolonged action.

In addition to the duration of action, the stability of the preparation is very important for patients. Stabilized insulin formulations having increased physical long-term stability are needed in particular for preparations, which are exposed to particular mechanical stresses or relatively high temperatures. These include, for example, insulins in administration systems such as pens, inhalation systems, needleless injection systems or insulin pumps. Insulin pumps are either worn on or implanted in the body of the patient. In both cases, the preparation is exposed to the heat of the body and movement and to the delivery motion of the pump and thus to a very high thermomechanical stress. Since insulin pens too (disposable and reutilizable pens) are usually worn on the body, the same applies here. Previous preparations have only a limited stability under these conditions.

Insulin is generally present in neutral solution in pharmaceutical concentration in the form of stabilized zinc-containing hexamers, which are composed of 3 identical dimer units (Brange et al., Diabetes Care 13:923-954 (1990)). However, the profile of action an insulin preparation may be improved by reducing the oligomeric state of the insulin it contains. By modification of the amino acid sequence, the self-association of insulin can be decreased. Thus, the insulin analog Lispro, for example, mainly exists as a monomer and is thereby absorbed more rapidly and shows a shorter duration of action (HPT Ammon and C. Werning; Antidiabetika [Antidiabetics]; 2. Ed.; Wiss. Verl.-Ges. Stuttgart; 2000; p. 94.f). However, the rapid-acting insulin analogs, which often exist in the monomeric or dimeric form, are less stable and more prone to aggregate under thermal and mechanical stress than hexameric insulin. This makes itself noticeable in cloudiness and precipitates of insoluble aggregates. (Bakaysa et al, U.S. Pat. No. 5,474,978). These higher molecular weight transformation products (dimers, trimers, polymers) and aggregates decrease not only the dose of insulin administered but can also induce irritation or immune reactions in patients. Moreover, such insoluble aggregates can affect and block the cannulas and tubing of the pumps or needles of pens. Since zinc leads to an additional stabilization of insulin through the formation of zinc-containing hexamers, zinc-free or low-zinc preparations of insulin and insulin analogs are particularly susceptible to instability. In particular, monomeric insulin analogs having a rapid onset of action are prone to aggregate and become physically unstable very rapidly, because the formation of insoluble aggregates proceeds via monomers of insulin.

In order to maintain the quality of an insulin preparation, it is necessary to avoid the formation of aggregates. There are various approaches for stabilizing insulin formulations. Thus, in international patent application WO98/56406, formulations stabilized by TRIS or arginine buffer have been described. U.S. Pat. No. 5,866,538 describes an insulin preparation that contains glycerol and sodium chloride in concentrations of 5-100 Mm and should have an increased stability. U.S. Pat. No. 5,948,751 describes insulin preparations having increased physical stability, which is achieved by addition of mannitol or similar sugars. The addition of excess zinc to a zinc-containing insulin solution can likewise increase the stability (J. Brange et al., Diabetic Medicine, 3: 532-536, 1986). The influence of the pH and various excipients on the stability of insulin preparations has also been described in detail (J. Brange & L. Langkjaer, Acta Pharm. Nordica 4: 149-158).

U.S. Pat. Nos. 7,476,652 and 7,713,930 discloses pharmaceutical formulations that comprise Gly(A21), Arg(B31), Arg(B32)-human insulin; at least one chemical entity chosen from esters and ethers of polyhydric alcohols; at least one preservative; and water, wherein the pharmaceutical formulation has a pH in the acidic range from 1 to 6.8. It has been further disclosed that non-ionic surfactants specifically esters and ethers of polyhydric alcohols (polysorbate 20 and polysorbate 80) increase the stability of acidic insulin preparations and thus preparations can be produced which have superior stability to hydrophobic aggregation nuclei for several months under temperature stress.

It has been also disclosed in several prior arts that surfactants can causes charge generation in polypeptide solutions and increase the aggregation process and make peptide formulations unstable in long term.

U.S. Pat. No. 5,866,538 discloses a pharmaceutical formulation comprising a polypeptide selected from the group consisting of human insulin, an analogue thereof, a derivative thereof, glycerol, mannitol, or glycerol & mannitol and 5 to 100 mM of a halogenide. It has been shown in the said patent that insulin preparations of superior chemical stability can be obtained in the presence of low halogenide concentrations. Further, Acta Pharmaceutica Nordica 4(4), 1992, pp. 149-158 discloses insulin preparations in which the sodium chloride (Halogenide) concentration has been varied in the range of 0 to 250 mM. However, the major part of the preparations, including all preparations contains a rather high amount of sodium chloride, i.e. 0.7% corresponding approximately to a concentration of 120 mM. It is stated in this document that sodium chloride generally has a stabilizing effect on insulin preparations; glycerol and glucose lead to increased chemical deterioration.

Numbers of attempts have been made till date to provide formulations comprising insulin that remain chemically stable for a sufficiently long period of time.

U.S. Pat. No. 4,476,118 discloses stable insulin solution comprising a preserving agent, an isotonicity agent, and a pH-buffering agent, which solution contains essentially ionized zinc.

U.S. Pat. Nos. 6,906,028 and 6,551,992, 6,034,054 discloses solution formulation comprising: a physiologically tolerated buffer selected from the group consisting of TRIS and arginine; a monomeric insulin analog wherein, the insulin analog is $Lys^{B28}$ $Pro^{B29}$-human insulin; zinc; and a phenolic preservative.

U.S. Pat. No. 6,174,856 discloses that the stability of insulin compositions can be significantly improved by formulating the compositions using a combination of a buffer such as glycylglycine (Gly-Gly) and metal ions such as $Ca^{2+}$.

U.S. Pat. No. 6,734,162 discloses a method of inhibiting aggregation of a polypeptide comprising combining the polypeptide with a buffer comprising tris(hydroxymethyl) aminomethane (TRIS) mixed with a buffering molecule that does not contain a free amine group and which mitigates the change in pH that results from the formation of carbonic acid; zinc; and a phenolic preservative for a time and under conditions effective to inhibit aggregation.

U.S. Pat. No. 6,737,401 discloses an unexpected property of the novel surfactant stabilized insulin formulations.

U.S. Pat. No. 8,263,551 discloses pharmaceutical formulations comprising insulin, insulin analogs, insulin derivatives or mixtures of the foregoing, and a salt of protamine where the protamine salt wherein protamine salt was used for increasing the physical and chemical stability of an insulin-containing formulation U.S. Pat. No. 8,097,584 discloses that pharmaceutical polypeptide formulations having increased chemical stability can be obtained by adding ethylenediamine or salts thereof as a buffer to said formulation.

US Patent Application No. 20090175840 discloses an injectable formulation comprising insulin, a diluent suitable for injection, an oxidizing agent or enzyme and a reducing agent or enzyme, with the proviso that the formulation does not contain a chitosan-glycerol phosphate hydrogel.

US Patent Application No. 20090325860 discloses an aqueous pharmaceutical formulation comprising an aqueous mixture of an insulin molecule, a solubilizing agent, a surface active agent, and a thickening agent, wherein the pharmaceutical formulation confers an ultra-rapid acting insulin profile to a non-ultra-rapid acting insulin.

US Patent Application No. 20100069292 discloses a basal insulin formulation comprising a solution of recombinant human insulin at a pH between 3.5 and 4.5, preferably 3.8 to 4.2, or 7.5 to 8.5, optionally in combination with a stabilizing agent, buffering agent and precipitating agent, but not including protamine.

US Patent Application 20120252724 discloses an aqueous pharmaceutical formulation comprising an insulin, insulin analog or insulin derivative, or a pharmacologically tolerable salt thereof, and methionine.

US Patent Application No. 20130011378 discloses a stable co-formulation comprising a therapeutically effective amt. of fast-acting insulin, a hyaluronan-degrading enzyme, NaCl, an antimicrobial preservative, and a stabilizing agents.

US Patent Application No. 20100203014 discloses a method for nasal administration of an acidic pharmaceutical composition to a subject comprising administering to the nasal mucosa of the subject a pharmaceutical composition comprising: i) a therapeutically active peptide; and ii) an aqueous solution buffered with a zwitterionic amino acid, wherein the composition has a pH of about 3.0 to 4.5, thereby administering the acidic pharmaceutical composition to the subject.

US Patent Application No. 20120094903 discloses a pharmaceutical formulation for intranasal delivery of insulin to a patient, comprising an aqueous mixture of human insulin, a solubilizing agent, a surface active agent, and a thickening agent, for nasal delivery.

Chinese Patent Application No. 101045158 discloses a pharmaceutical composition comprising insulin analog, and medical adjuvant containing sugar, organic salt, amino acid, and protein.

IN Patent Application No. 2008MUM01454 discloses an insulin analog protamine crystals comprising human insulin analog, zinc ions, protamine and one or more ligand selected from group consisting of benzyl alcohol, phenylethanol, phenoxyethanol, benzoic acid, mandelic acid, 2,2,2-trifluoro-1-phenylethanol, phenylphosphonic acid and derivatives thereof.

PCT Publication No. 2001000312 discloses systems and methods for manufacturing dry powder formulations.

PCT Publication No. 2012066086 A1 discloses a pharmaceutical formulation comprising insulin glargine and Sulfobutyl Ether 7-[beta]-cyclodextrin.

PCT Publication No. 2007/041481 discloses a formulation comprising intermediate or a long acting insulin, and long acting insulin with an effective amount of a chelator and an acidifying agent to enhance the rate or amount of uptake by a patient.

PCT Publication No. 2010149772 discloses composition comprising an insulin compound or a mixture of two or more insulin compounds, a nicotinic compound and an amino acid.

Several attempts to provide stable insulin, insulin analogs and derivatives formulations have been described previously. However, there still exists a need to develop formulations wherein the insulin does not undergo chemical transformation, and remains stable for a sufficiently long period of time.

Surprisingly, the inventors of present invention found that the insulin preparations having better solubility and chemical stability can be obtained in the presence of solubility-enhancing agent selected from urea, amino acids and/or surfactants with a pH modifying agents other than halogenides.

SUMMARY OF THE INVENTION

The term "insulin(s)" used herein includes mammalian insulin, insulin analogues or derivatives.

The term "Insulin analogs" used in the present invention includes analogs of naturally occurring insulins, namely human insulin or animal insulins, which differ by substitution of at least one naturally occurring amino acid residue with other amino acid residues and/or addition/removal of at least one amino acid residue from the corresponding, otherwise identical, naturally occurring insulin. The added and/or replaced amino acid residues can also be those, which do not occur naturally.

The term "Insulin derivatives" used in the present invention includes derivatives of naturally occurring insulin or of an insulin analog, which are obtained by chemical modification. The chemical modification can consist, for example, in the addition, substitution or deletion of one or more specific chemical groups to one or more amino acids. It can also involve the addition, substitution or deletion of one or more chemical groups of the peptide backbone, such as, at the amino and/or carboxyl terminus.

By "analogue of human insulin" as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" as used herein is meant human insulin or an analogue thereof in which at least one organic substituent is bound to one or more of the amino acids.

By "halogenide" as used herein is meant a binary compound, of which one part is a halogen atom and the other part is an element or radical that is less electronegative than halogen atom e.g. an alkali or alkaline earth metal halogenide, e.g. a chloride such as sodium chloride.

By "Complexing agents" as used herein is meant a molecule that has a multiplicity of charges and that binds to or complexes with insulin compound conjugates. Examples of complexing agents suitable for use in the present invention include protamines, surfen, globin proteins, spermine, spermidine albumin, carboxylic acids, polycationic polymer compounds, cationic polypeptides, anionic polypeptides, nucleotides, and antisense. See Brange, J., Galenics of Insulin compound, Springer-Verlag, Berlin Heidelberg (1987), the entire disclosure of which is incorporated herein by reference.

By "devoid of complexing agent" as used herein is meant said complexing agent is present in a concentration less than of 0.01% w/v of the total composition.

One of the aspects of the present invention provides a stable aqueous pharmaceutical composition comprising human insulin, analogues or derivatives thereof, a solubility-enhancing agent selected from urea, amino acids and/or surfactants, and optionally one or more other pharmaceutically acceptable excipient(s).

Another aspect of the present invention provides a stable aqueous pharmaceutical composition comprising human insulin, analogues or derivatives thereof, a solubility-enhancing agent selected from urea, amino acids and/or surfactants, and optionally one or more other pharmaceutically acceptable excipient(s), wherein the pharmaceutical composition is devoid of complexing agents.

Another aspect of the present invention provides a stable aqueous pharmaceutical composition comprising human insulin, analogues or derivatives thereof, a solubility-enhancing agent selected from urea, amino acids and/or surfactants, and a pH modifying agent optionally one or more other pharmaceutically acceptable excipient(s), wherein the pH modifying agent is other than halogenide.

Another aspect of the present invention provides a stable aqueous pharmaceutical composition comprising $Asp^{B28}$ human insulin, a solubility-enhancing agent selected from urea, amino acids and/or surfactants, one or more pH modifying agent and optionally one or more other pharmaceutically acceptable excipient(s), wherein the pH modifying agent is other than halogenide.

Another aspect of the invention provides a stable aqueous pharmaceutical composition comprising human insulin, analogues or derivatives thereof, a pH modifying agent other than halogenides, and optionally one or more other pharmaceutically acceptable excipient(s).

Another aspect of the invention provides a stable aqueous pharmaceutical composition comprising human insulin, analogues or derivatives thereof, a solubility-enhancing agent selected from urea, amino acids and/or surfactants, a pH modifying agent, and optionally one or more other pharmaceutically acceptable excipient(s).

Another aspect of the invention is to provide a stable aqueous pharmaceutical composition comprising human insulin, analogues or derivatives thereof, a pH modifying agent other than halogenides wherein the pH of the dosage form is between 6.8 to 7.6, and optionally one or more other pharmaceutically acceptable excipient(s).

Another aspect of the invention provides a stable aqueous pharmaceutical composition comprising human insulin, analogues or derivatives thereof, a solubility-enhancing agent selected from urea, amino acids and/or surfactants, a pH modifying agent wherein the pH of the dosage form is between 6.8 to 7.6, and optionally one or more other pharmaceutically acceptable excipient(s).

Another aspect of the present invention provides a stable aqueous pharmaceutical composition comprising $Asp^{B28}$ human insulin, one or more amino acids as a solubility-enhancing agent, a pH modifying agent other than halogenides and optionally one or more other pharmaceutically acceptable excipient(s).

It is another aspect of the present invention to provide process for preparation of such composition, wherein said process comprises of:
a) preparing a solution comprising solubility-enhancing agent along with other pharmaceutically acceptable excipients,
b) separately preparing the insulin solution and optionally adding the pH modifying agent to it,
c) mixing the solutions of step a) & b).

Yet another aspect of the present invention provides a method of using such composition to achieve a therapeutic effect, which comprises administering to a subject in need thereof an effective amount of the composition.

It is another aspect of the invention to provide a pharmaceutical composition comprising Gly(A21), Arg(B31), Arg (B32)-human insulin; a solubilizer; and optionally one or more other pharmaceutically acceptable excipient(s).

The Gly(A21), Arg(B31), Arg(B32)-human insulin generically known as Insulin glargine. Currently insulin glargine is marketed by Sanofi under the brand name of "Lantus" & by Wockhardt under the brand name of "Glaritus".

Another aspect of the invention is to provide a pharmaceutical composition comprising a Gly(A21), Arg(B31), Arg(B32)-human insulin; a solubilizer selected from urea, amino acids, cationic surfactants, anionic surfactants or amphoteric surfactant; and optionally one or more other pharmaceutically acceptable excipient(s).

Another aspect of the invention is to provide a pharmaceutical composition comprising a Gly(A21), Arg(B31), Arg(B32)-human insulin; a solubilizer selected from urea, amino acids, cationic surfactants, anionic surfactants or amphoteric surfactant; pH modifying agent; and optionally one or more other pharmaceutically acceptable excipient(s), wherein said composition has a pH is between 3.9-4.2.

Another aspect of the invention is to provide a pharmaceutical composition comprising a Gly(A21), Arg(B31), Arg(B32)-human insulin, one or more amino acids, pH modifying agent; and optionally one or more other pharmaceutically acceptable excipient(s), wherein said composition has a pH is between 3.9-4.2.

It is another aspect of the present invention to provide process for preparation of such composition, which comprises of:
a. preparing a solution comprising pH modifying agent,
b. preparing an insulin solution by dissolving insulin in acidic water for injection,
c. preparing a solution of solubilizer selected from urea, amino acids, cationic surfactants, anionic surfactants or amphoteric surfactant,
d. mixing the solution of step (a) with the solution of step (b),
e. adding solution of step (c) to the solution of step (d).

It is yet another aspect of the present invention to provide a method for controlling the level of glucose in a patient suffering from diabetes by administering to the subject pharmaceutical compositions of the present invention.

DETAILED DESCRIPTION OF THE INVENTION

The inventors of present invention have surprisingly found that solubility-enhancing agent selected from urea, amino acids, cationic surfactants, anionic surfactants or amphoteric surfactant can provide the stable long acting composition of insulin glargine with better solubility and chemical stability. Further, the inventors of present invention surprisingly found that the stable insulin preparations can be obtained in the presence of cationic, anionic, amphoteric surfactant by modifying various conditions in contrast to the disclosure of prior arts.

The present inventors have found that the amino acid as solubility-enhancing agent not only increase solubility of the insulins but also helps in thermodynamically stabilizing the insulins by keeping them in their native state. The formulations comprising insulin glargine or aspart and one or more amino acids were found to stable and free from aggregates even when surfactants were not present in the formulation.

The present invention provides a stable aqueous composition comprising human insulin, analogues or derivatives thereof and other pharmaceutically acceptable excipient(s).

In one aspect of the present invention, there is provided a stable aqueous pharmaceutical composition comprising human insulin, analogues or derivatives thereof, one or more solubility-enhancing agent selected from amino acids and/or surfactants, and optionally one or more other pharmaceutically acceptable excipient(s).

The insulin analogues used in the present invention include, but not limited to, an analogues wherein position B28 is Asp, Lys, Leu, Val or Ala; position B29 is Lys or Pro; or des(B28-B30), des(B27) or des(B30) human insulin or A21 is Gly and Arg has been added to B31 and B32; or where the amino acid residues in B28-B30 have been deleted; or where the amino acid residue at B27 has been deleted; or where the amino acid residue at B30 has been deleted. Marketed Insulin analogues include but are not limited to Insulin aspart ($Asp^{B28}$ human insulin), Insulin Lispro ($Lys^{B28}$ $Pro^{B29}$ human insulin), Insulin glulisine, Insulin glargine ($Gly^{A21} Arg^{B31} Arg^{B32}$-human insulin or Gly (A21), Arg(B31), Arg(B32)-human insulin), etc.

The insulin derivatives used in the present invention include, but not limited to, B29-Nϵ-myristoyl-des(B30) human insulin, B29-Nϵ-palmitoyl-des(B30) human insulin, B29-Nϵ-myristoyl human insulin, B29-Nϵ-palmitoyl human insulin, B28-Nϵ-myristoyl $Lys^{B28}$ $Pro^{B29}$ human insulin, B28-Nϵ-palmitoyl $Lys^{B28}$ $Pro^{B29}$ human insulin, B30-Nϵ-myristoyl-$Thr^{B29}$ $Lys^{B30}$ human insulin, B30-Nϵ-palmitoyl-$Thr^{B29}$ $Lys^{B30}$ human insulin, B29-Nϵ-(N-palmitoyl-γ-glutamyl)-des(B30) human insulin, B29-Nϵ-(N-lithocholyl-γ-glutamyl)-des(B30) human insulin, B29-Nϵ-carboxyheptadecanoyl)-des(B30) human insulin and-B29-Nϵ-(ω-carboxyhept adecanoyl) human insulin.

In one aspect of the present invention, there is provided a stable aqueous pharmaceutical composition comprising human insulin, analogues or derivatives thereof, one or more solubility-enhancing agent selected from amino acids and/or surfactants, and optionally one or more other pharmaceutically acceptable excipient(s), wherein the human insulin, analogues or derivatives thereof is selected from one or more of recombinant human insulin, Insulin NPH, Insulin Lispro, Insulin Lispro Protamine, Insulin Glulisine and Insulin Aspart, Insulin Aspart Protamine, Insulin glargine, and insulin detemir.

In one aspect of the present invention, there is provided a stable aqueous pharmaceutical composition comprising $Asp^{B28}$-human insulin, one or more amino acid as solubility-enhancing agent and/or surfactants, and optionally one or more other pharmaceutically acceptable excipient(s).

The pH of the pharmaceutical composition of the invention is between 2-8.

In one aspect of the present invention, there is provided a stable aqueous pharmaceutical composition comprising human insulin, analogues or derivatives thereof, a pH modifying agent and optionally one or more other pharmaceutically acceptable excipient(s), wherein the pH modifying agent is other than halogenide.

In one aspect of the present invention, there is provided a stable aqueous pharmaceutical composition comprising human insulin, analogues or derivatives thereof, a pH modifying agent other than halogenides and optionally one or more other pharmaceutically acceptable excipient(s), wherein the human insulin, analogues or derivatives thereof is selected from one or more of recombinant human insulin, Insulin NPH, Insulin Lispro, Insulin Lispro Protamine, Insulin Glulisine and Insulin Aspart, Insulin Aspart Protamine, Insulin glargine, and insulin detemir.

In one aspect of the present invention, there is provided a stable aqueous composition comprising $Asp^{B28}$ human insulin, a pH modifying agent other than halogenides, and optionally one or more other pharmaceutically acceptable excipient(s).

In one aspect of the present invention, there is provided a stable aqueous pharmaceutical composition comprising human insulin, analogs, or derivatives thereof, a pH modifying agent other than halogenides wherein the pH of the dosage form is between 6.8 to 7.6, and optionally one or more other pharmaceutically acceptable excipient(s), wherein the human insulin, analogs, or derivatives thereof is selected from one or more of recombinant human insulin, Insulin NPH, Insulin Lispro, Insulin Lispro Protamine, Insulin Glulisine and Insulin Aspart, Insulin Aspart Protamine, Insulin glargine, and insulin detemir.

In one aspect of the present invention, there is provided a stable aqueous composition comprising $Asp^{B28}$ human insulin, a pH modifying agent other than halogenides wherein the pH of the dosage form is between 6.8 to 7.6, and optionally one or more other pharmaceutically acceptable excipient(s).

In one aspect of the present invention, there is provided a stable aqueous pharmaceutical composition comprising human insulin, analogs, or derivatives thereof, a solubility-enhancing agent selected from urea, amino acids and/or surfactants, a pH modifying agent other than halogenides, and optionally one or more other pharmaceutically acceptable excipient(s), wherein the human insulin, analogs, or derivatives thereof is selected from one or more of recombinant human insulin, Insulin NPH, Insulin Lispro, Insulin Lispro Protamine, Insulin Glulisine and Insulin Aspart, Insulin Aspart Protamine, Insulin glargine, and insulin detemir.

In one aspect of the present invention, there is provided a stable aqueous pharmaceutical composition comprising $Asp^{B28}$ human insulin, a solubility-enhancing agent selected from urea, amino acids and/or surfactants, a pH modifying agent other than halogenides, and optionally one or more other pharmaceutically acceptable excipient(s).

In yet another aspect of the present invention, there is provided a stable aqueous composition comprising human insulin, analogues or derivatives thereof, amino acids as a solubility-enhancing agent, a pH modifying agent other than halogenides wherein the pH of the dosage form is between 6.8 to 7.6, and optionally one or more other pharmaceutically acceptable excipient(s).

In yet another aspect of the present invention, there is provided a stable aqueous composition comprising human insulin, analogues or derivatives thereof, surfactants as a solubility-enhancing agent, a pH modifying agent other than halogenides wherein, the pH of the dosage form is between 6.8 to 7.6, and optionally one or more pharmaceutically acceptable excipient(s).

In another aspect of the present invention, there is provided a stable aqueous composition comprising $Asp^{B28}$-human insulin, arginine, m-cresol, phenol, glycerol, zinc and a pH modifying agent other than halogenide.

In another aspect of the present invention, there is provided a method for improving the stability of pharmaceutical compositions comprising human insulin, analogues or derivatives thereof, wherein the method comprises adding one or more solubility-enhancing agent selected from the group consisting of urea, amino acids and/or surfactants to the composition.

In another aspect of the present invention, there is provided a method for improving the stability of pharmaceutical compositions comprising human insulin, analogues or derivatives thereof, wherein the method comprises adding one or more amino acids to the composition for solubilizing and stabilizing the human insulin, analogues or derivatives thereof.

The present invention provides a pharmaceutical composition comprising Gly(A21), Arg(B31), Arg(B32)-human insulin; a solubility enhancing agent; and optionally one or more other pharmaceutically acceptable excipient(s).

In one aspect of the invention, there is provided a pharmaceutical composition comprising Gly(A21), Arg(B31), Arg(B32)-human insulin; one or more solubility enhancing agents selected from urea, amino acids, cationic surfactants, anionic surfactants or amphoteric surfactant; and optionally one or more other pharmaceutically acceptable excipient(s).

In another aspect of the invention, there is provided a pharmaceutical composition comprising Gly(A21), Arg (B31), Arg(B32)-human insulin; one or more a solubility enhancing agent selected from urea, amino acids, cationic surfactants, anionic surfactants or amphoteric surfactant; pH modifying agent; and optionally one or more other pharmaceutically acceptable excipient(s); wherein said composition has a pH is between 3.9-4.2.

The amino acids used for the present invention includes but are not limited to, glycine, arginine, histidine, lysine, serine, threonine, aspartic acid, glutamic acid, serine, threonine, glutamine, asparagine, alanine, isoleucine, leucine or salts thereof.

The amino acids used for the present invention include glycine, arginine, histidine or salts thereof.

In another aspect of the invention, there is provided a pharmaceutical composition comprising Gly(A21), Arg (B31), Arg(B32)-human insulin; glycine, m-cresol, zinc, glycerol and pH modifying agent(s); and optionally one or more other pharmaceutically acceptable excipient(s); wherein said composition has a pH is between 3.9-4.2.

The amino acids used in the present invention not only helps in solubilizing the active agent but also helps in stabilizing the molecule by keeping the molecule in thermodynamically stable native state.

For the purpose of present invention, surfactants may be selected from the group comprising but not limited to polyethylene glycol-polypropylene glycol copolymer, benzalkonium salts, polyoxyalkylene alkylamines, alkylamines, alkanolamine fatty acid esters, quaternary ammonium fatty acid esters, dialkyl ammonium salts, alkyl pyridinium salts including stearylamine, triethanolamine oleate, benzethonium chloride, sodium lauryl sulfonate, ammonium lauryl sulfonate, dodecyl benzene sulfonate, sodium lauryl ether sulfate, diethanolamine lauryl sulfate, ammonium salts of sulfated alcohol ethoxylates, sodium cocoyl isethionate, sodium N-methyl-N-oleoyl taurate, sodium N-methyl-N-cocoyl taurate, triethanolamine lauryl sulfate, disodium monooleamide PEG-2 sulfosuccinate, petroleum sulfonates sodium salt, alkyl napthalene sodium sulfonates, sodium lauroyl sarcosinate, or sodium alkyl sulfosuccinate, alkyl beta aminopropionates, 2-alkylimidazoline quaternary ammonium salts, ricinoleamidopropyl betaine, cocamidopropyl betaine, stearyl betaine, stearyl amphocarboxy glycinate, sodium lauraminopropionate, cocoamidopropyl hydroxy sultaine, disodium lauryliminodipropionate, tallowiminodipropionate, cocoampho-carboxy glycinate, cocoimidazoline carboxylate, lauric imidazoline monocarboxylate, lauric imidazoline dicarboxylate, lauric myristic betaine, cocoamidosulfobetaine, alkylamidophospho betaine, lecithins and hydrogenated lecithins; lysolecithins and hydrogenated lysolecithins; phospholipids and derivatives thereof; or lysophospholipids and derivatives thereof.

The surfactant used for the purpose of present invention is the polyethylene glycol-polypropylene glycol copolymer. The polyethylene glycol-polypropylene glycol copolymer used is Synperonic®F108; Synperonic®L121; Synperonic®L122; Synperonic®P105; Synperonic®P85; Synperonic®F68; SynperonicPe®/L61; Synperonic®F108; Synperonic®F68; Synperonic® L61; Synperonic®/L64; Poloxamer®118; Poloxamer®124; Poloxamer®181; Poloxamer®182; Poloxamer®184; Poloxamer®188; Poloxamer®237; Poloxamer®331; Poloxamer®338; Pluronic Polyol F-68® or combination thereof.

The pH modifying agents used for the purpose of present invention is a combination of acid and alkali, wherein pH modifying agent is other than halogenides, wherein acid is selected form the group comprising of o-phosphoric acid, citric acid, acetic acid, succinic acid, lactic acid, gluconic acid, tartaric acid, 1,2,3,4-butane tetracarboxylic acid, fumaric acid or malic acid Alkali is selected form the group comprising of sodium hydroxide, potassium hydroxide, sodium hydroxide, ammonium hydroxide, magnesium oxide, calcium hydroxide, calcium carbonate, magnesium carbonate, magnesium aluminum silicates, diethanolamine, monoethanolamine, sodium carbonate, sodium bicarbonate or triethanolamine.

The pharmaceutically acceptable excipients include, but are not limited to, preservatives, isotonicity agents or diluent.

The "preservative" as used herein refers to that can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, m-cresol or combinations thereof.

An "isotonicity agent" is a compound that is physiologically tolerated and imparts a suitable tonicity to a formulation to prevent the net flow of water across cell membranes that are in contact with the formulation. Compounds, such as glycerin, are commonly used for such purposes at known concentrations. Other possible isotonicity agents include salts, e.g., sodium chloride, dextrose, or lactose.

Typically the insulin is dissolved or dispersed in a diluent to provide the insulin in a liquid form. Suitable diluents include, but are not limited to, water, buffered aqueous solutions, dilute acids, vegetable or inert oils for injection organic hydrophilic diluents, such as monovalent alcohols, and low molecular weight glycols and polyols (e.g. propylene glycol, polypropylene glycol, glycerol, and butylene glycol).

The pharmaceutical inventions of the present invention are intended for or Injectable administration.

The pharmaceutical inventions of the present invention are intended for subcutaneous, intramuscular or intravenous administration.

In the present invention, there is provided a process for preparation of a insulin composition, wherein said process comprises of:
a) preparing a solution comprising solubility-enhancing agent along with other pharmaceutically acceptable excipients,
b) separately preparing the insulin solution and addition of pH modifying agent to it,
c) mixing the solutions of step a) & b).

The final volume is made up with the help of water for injection (WFI). The pH is adjusted with pH modifying agents.

In another aspect of the present invention, there is provided a process for preparation of a insulin formulation involving the following steps:
a) preparing a solution comprising pH modifying agent,
b) preparing an insulin solution by dissolving insulin in acidic water for injection,
c) preparing a solution of solubilizer selected from urea, amino acids, cationic surfactants, anionic surfactants or amphoteric surfactant, d) mixing the solution of step (a) with the solution of step (b),
e) adding solution of step (c) to the solution of step (d).

The final volume is made up with the help of water for injection (WFI). The pH is adjusted with pH modifying agents.

The said insulin composition has a high chemical stability, which is reflected in a reduction in the formation of dimers and polymers and desamido insulins after storage. Furthermore, the physical stability is not deteriorated by the absence of the halogenide (which is termed as a stabilizer in the prior arts), and the insulin does not precipitate by long-term storage of the insulin preparations.

In another aspect of the present invention, there is provided a method for treating diabetes comprising administering a pharmaceutical composition of the present invention to the patient in need thereof.

In another aspect of the present invention, there is provided a method for controlling the level of glucose in a patient suffering from diabetes comprising administering to the patient a pharmaceutical composition of the present invention.

The examples given below serve to illustrate embodiments of the present invention. However they do not intend to limit the scope of present invention.

Example-1

| S. No. | Ingredients | Qty (mg/mL) |
|---|---|---|
| 1 | Insulin Aspart | 100 IU |
| 2 | Phenol | 1-2 |
| 3 | m-Cresol | 1-2.5 |
| 4 | Glycine | 1-1.5 |
| 5 | Zinc Chloride | 0.0196 |
| 6 | Disodium Hydrogen Phosphate Dihydrate | 1-2.5 |
| 7 | Sodium Hydroxide | Q.S. |
| 8 | Ortho-phosphoric acid | Q.S. |
| 9 | Water For Injection (WFI) | Q.S. |
| 10 | Sodium sulfate | 0.1-2.0 |

Example-2

| S. No. | Ingredients | Qty (mg/mL) |
|---|---|---|
| 1 | Insulin | 100 IU |
| 2 | Phenol | 1-2 |
| 3 | m-Cresol | 1-2.5 |
| 4 | Glycine | 1-1.5 |
| 5 | Zinc Chloride | 0.0196 |
| 6 | Disodium Hydrogen Phosphate Dihydrate | 1-2.5 |
| 7 | Sodium Hydroxide | Q.S. |
| 8 | Hydrochloric acid | Q.S. |
| 9 | Water For Injection (WFI) | Q.S. |
| 10 | Sodium sulfate | 0.1-2.0 |

Example-3

| S. No. | Ingredients | Qty (mg/mL) |
|---|---|---|
| 1. | Insulin | 100 IU |
| 2. | Phenol | 1-2 |
| 3. | m-Cresol | 1-2.5 |
| 4. | Glycerol | 5-20 |
| 5. | Sodium sulfate | 0.1-2.0 |
| 6. | Zinc Chloride | 0.0196 |
| 7. | Sodium Hydroxide | Q.S. |
| 8. | Ortho phosphoric acid | Q.S. |
| 9. | Disodium Hydrogen Phosphate Dihydrate | 1.25 |
| 10. | Water For Injection (WFI) | Q.S. |

Example-4

| S. No. | Ingredients | Qty (mg/mL) |
|---|---|---|
| 1 | Insulin Aspart | 100 IU |
| 2 | Phenol | 1-2 |
| 3 | m-Cresol | 1-2.5 |
| 4 | Histidine | 1-2 |
| 5 | Zinc Chloride | 0.0196 |
| 6 | Sodium Hydroxide | Q.S. |
| 7 | Hydrochloric acid | Q.S. |
| 8 | Disodium Hydrogen Phosphate Dihydrate | 1.25 |
| 9 | Water For Injection (WFI) | Q.S. |

Example-5

| S. No. | Ingredients | Qty (mg/mL) |
|---|---|---|
| 1 | Insulin | 100 IU |
| 2 | Phenol | 1-2 |
| 3 | m-Cresol | 1-2.5 |
| 4 | Arginine | 1-2 |
| 5 | Poloxamer 188 | 0.05-4 |
| 6 | Zinc Chloride | 0.0196 |
| 7 | Sodium Hydroxide | Q.S. |
| 8 | Hydrochloric acid | Q.S. |
| 9 | Disodium Hydrogen Phosphate Dihydrate | 1.25 |
| 10 | Water For Injection (WFI) | Q.S. |

Example-6

| S. No. | Ingredients | Qty (mg/mL) |
|---|---|---|
| 1 | Insulin Aspart | 100 IU |
| 2 | Phenol | 1-2 |
| 3 | m-Cresol | 1-2.5 |
| 4 | Arginine | 1-2.5 |
| 5 | Glycerol | 5-20 |
| 6 | Zinc Chloride | 0.0196 |
| 7 | Sodium Hydroxide | Q.S. |
| 8 | Hydrochloric acid | Q.S. |
| 9 | Disodium Hydrogen Phosphate Dihydrate | 1.25 |
| 10 | Water For Injection (WFI) | Q.S. |

Procedure:

The pharmaceutical compositions described in Example 1 to 6 were prepared according to the process detailed below.

Step 1: Buffer Preparation
Buffer Solution:
The m-cresol (distilled), phenol, and/or glycerol, one or more solubility enhancing agents Glycine/Arginine/Histidine/Glycerol/Poloxamer as per examples, sodium sulphate and/or disodium hydrogen o-phosphate dihydrate are dissolved in water for injection (WFI) one after another to prepare buffer solution.

Preparation of Zinc Chloride (1% w/v) Solution:
Accurately weighed 208 mg Zinc chloride was dissolved in 10 ml of WFI.

Step 2: Preparation of API Solution
Preparation of API Solution:
Accurately weighed Insulin or Insulin Aspart was dispersed in WFI. To it added zinc chloride solution (1% w/v) (quantity calculated based on endogenous zinc content of API) in sufficient quantity to form paste. To the above paste o-Phosphoric acid or hydrochloric acid was added in sufficient quantity to form a clear solution. Final volume of this solution was made up by WFI.

Step 3: Final Solution
The API solution was mixed with buffer solution. The pH of the solution was adjusted with 10% v/v o-Phosphoric acid or 10% w/v NaOH or hydrochloric acid to pH 2.9-3.4 first and then to pH 7.2 to 7.4. The final solution was filtered through 0.2µ syringe filter in another 50.0 mL Falcon tube under LAF.

Example 7

| S. No. | Ingredients | Qty/mL |
|---|---|---|
| 1. | Insulin Glargine (r-DNA) | 100.0 IU |
| 2. | m-Cresol | 1-4 mg |
| 4. | Glycerol (85%) | 5-40 mg |
| 5. | Zinc as Zinc Chloride | 0.03 mg |
| 7. | Sodium Hydroxide | Q.S. to pH |
| 8. | Hydrochloric acid | Q.S. to pH |
| 9. | Water For Injection (WFI) | Q.S. to 1.0 ml |
| 10. | Arginine | 01-2.5 mg |

Procedure:
Buffer solution is prepared by dissolving m-Cresol and Glycerol (85%) in WFI. A 1% w/v solution of Zinc chloride is prepared by dissolving zinc chloride in water. API solution is prepared by dissolving Insulin glargine in acidic WFI. To this API solution, 1% % w/v solution of Zinc chloride is added to form a paste. A 10% v/v hydrochloride solution was added to form a clear solution. To this clear solution, buffer solution and arginine solution was added. The pH of the solution was adjusted between 3.9-4.2 with 10% v/v NaOH.

Example 8

| S. No. | Ingredients | Qty/mL |
|---|---|---|
| 1. | Insulin Glargine (r-DNA) | 100.0 IU |
| 2. | m-Cresol | 1-4 mg |
| 4. | Glycerol (85%) | 5-40 mg |
| 5. | Zinc as Zinc Chloride | 0.03 mg |
| 7. | Sodium Hydroxide | Q.S. to pH |
| 8. | Hydrochloric acid | Q.S. to pH |
| 9. | Water For Injection | Q.S. to 1.0 ml |
| 10. | Histidine HCl | 0.1-2.5 mg |

Procedure:
Buffer solution is prepared by dissolving m-Cresol and Glycerol (85%) in WFI. A 1% w/v solution of Zinc chloride is prepared by dissolving zinc chloride in water. API solution is prepared by dissolving Insulin glargine in acidic WFI. To this API solution, 1% % w/v solution of Zinc chloride was added to form a paste. A 10% v/v hydrochloride solution was added to form a clear solution. To this clear solution, buffer solution and histidine hydrochloride solution were added. The pH of the solution was adjusted between 3.9-4.2 with 10% v/v NaOH.

Example 9

| S. No. | Ingredients | Qty/mL |
|---|---|---|
| 1. | Insulin Glargine (r-DNA) | 100.0 IU |
| 2. | m-Cresol | 1-4 mg |
| 4. | Glycerol (85%) | 5-40 mg |
| 5. | Zinc as Zinc Chloride | 0.03 mg |
| 7. | Sodium Hydroxide | Q.S. to pH |
| 8. | o-phosphoric acid | Q.S. to pH |
| 9. | Water For Injection | Q.S. to 1.0 ml |
| 10. | Glycine | 0.1-2.5 |

Procedure:
Buffer solution is prepared by dissolving m-Cresol and Glycerol (85%) in WFI. A 1% w/v solution of Zinc chloride is prepared by dissolving zinc chloride in water. API solution is prepared by dissolving Insulin glargine in acidic WFI. To this API solution, 1% w/v solution of Zinc chloride was added to form a paste. To it added o-phosphoric acid to dissolve the API. To this API solution, buffer solution and a solution glycine were added. The pH of the final solution was adjusted between 3.9-4.2 with 10% w/v NaOH.

Example 10

| S. No. | Ingredients | Qty/mL |
|---|---|---|
| 1. | Insulin Glargine (r-DNA) | 100.0 IU |
| 2. | Phenol | 1-4 mg |
| 4. | Glycerol (85%) | 5-40 mg |
| 5. | Zinc as Zinc Chloride | 0.03 mg |
| 7. | Sodium Hydroxide | Q.S. to pH |
| 8. | o-phosphoric acid | Q.S. to pH |
| 9. | Water For Injection | Q.S. to 1.0 ml |
| 10. | Phospholipids | 0.01-10 mg |

Procedure:
Buffer solution is prepared by dissolving phenol and glycerol (85%) in WFI. A 1% w/v solution of Zinc chloride is prepared by dissolving zinc chloride in water. API solution is prepared by dissolving Insulin glargine in acidic WFI. To this API solution, 1% w/v solution of Zinc chloride is added to form a paste. To it added o-phosphoric acid to dissolve the API. To this API solution, buffer solution and phospholipids solution were added. The pH of the final solution was adjusted between 3.9-4.2 with 10% w/v NaOH.

Example 11

| S. No. | Ingredients | Qty/mL |
|---|---|---|
| 1. | Insulin Glargine (r-DNA) | 100.0 IU |
| 2. | Phenol | 1-4 mg |
| 4. | Glycerol (85%) | 5-40 mg |
| 5. | Zinc as Zinc Chloride* | 0.03 mg |

| S. No. | Ingredients | Qty/mL |
| --- | --- | --- |
| 7. | Potassium Hydroxide | Q.S. to pH |
| 8. | Acetic acid | Q.S. to pH |
| 9. | Water For Injection | Q.S. to 1.0 ml |
| 10. | Urea | 0.1-4 mg |

Procedure:

Buffer solution is prepared by dissolving phenol and glycerol (85%) in WFI. A 1% w/v solution of Zinc chloride is prepared by dissolving zinc chloride in water. API solution is prepared by dissolving Insulin glargine in acidic WFI. To this API solution, 1% w/v solution of Zinc chloride is added to form a paste. To it added o-phosphoric acid to dissolve the API. To this API solution, buffer solution and urea solution were added. The pH of the final solution was adjusted between 3.9-4.2 with 10% w/v KOH.

Example 11

| S. No. | Ingredients | Qty/mL |
| --- | --- | --- |
| 1. | Insulin Glargine (r-DNA) | 100.0 IU |
| 2. | m-cresol | 1-4 mg |
| 3. | Glycerol (85%) | 5-40 mg |
| 4. | Zinc as Zinc Chloride | 0.02-0.04 mg |
| 5. | Glycine | 0.5-2.0 mg |
| 6. | Sodium Hydroxide | Q.S. to pH |
| 7. | Hydrochloric acid | Q.S. to pH |
| 8. | Water For Injection | Q.S. to 1.0 ml |

Procedure:

Step 1:

A solution of Insulin Glargine at 200 IU/mL concentration was prepared by dissolving zinc-containing crystals of Insulin Glargine in water for injection with the help of few μL of 1M HCl. The endogenous zinc level was supplemented by adding appropriate volume of zinc chloride solution (1% w/v).

Step 2:

Another solution of preservative/stabilizer system (2×) was prepared by dissolving m-Cresol, Glycerol and Glycine.

Step 3:

Both insulin solution of step 1 and solution of step 2 were diluted to final concentrations after mixing and pH adjustment to 4.0±0.2 with 1M HCl or 1M NaOH. The final formulation was then filtered through 0.2 filters. After sterile filtration, these preparations were introduced into vials and subjected to stability testing Stability Studies:

The pharmaceutical composition according to Example 6 of the present inventions were subjected to real time (5° C.±3° C.) and accelerated stability conditions at 25° C.±2° C. and 60% RH±5%. Samples were withdrawn initially and after 3 months and subjected to HPLC analysis.

| Stability Conditions | | Real Time Stability (5° C. ± 3° C.) 3 Months | Accelerated Stability (25° C. ± 2° C. and 60% RH ± 5%) 3 Months |
| --- | --- | --- | --- |
| Formulation & Batch No. | | Aspart R | Aspart R |
| Stabilizer & its Level | | L-Arginine (10 mM) | L-Arginine (10 mM) |
| Osmolality (mOsm/Kg) | | 259 | 259 |
| % HMWP | Initial | 0.14 | 0.14 |
| | 3 Months | 0.23 | 0.74 |
| % B-28 IsoAsp | Initial | 0.07 | 0.07 |
| | 3 Months | 0.16 | 1.96 |
| % B-3 + A-21 Asp | Initial | 0.4 | 0.4 |
| | 3 Months | 0.45 | 0.86 |
| % B-3 IsoAsp | Initial | 0 | 0 |
| | 3 Months | 0 | 0.77 |
| % Other Impurities | Initial | 0.32 | 0.32 |
| | 3 Months | 0.41 | 2.71 |

As evident from the stability, there is statistically insignificant increase in high molecular weight impurities (% HMWP), thus the API remains sufficiently in monomeric state. Further, the impurity level in the formulation has not increased significantly with time even on accelerated conditions. This implies that the compositions of present invention are stable even at accelerated conditions.

The invention claimed is:

1. A stable aqueous pharmaceutical composition comprising insulin glargine, a solubility-enhancing agent, one or more pH modifying agent(s), and optionally one or more other pharmaceutically acceptable excipient(s), wherein the solubility-enhancing agent is urea or glycine, and the glycine, when present, is present at about 0.1 mg/ml to about 2.5 mg/ml.

2. The pharmaceutical composition according to claim 1, wherein the pharmaceutical composition further comprises a surfactant selected from the group consisting of polyethylene glycol-polypropylene glycol copolymer, benzalkonium salts, polyoxyalkylene alkylamines, alkylamines, alkanolamine fatty acid esters, quaternary ammonium fatty acid esters, dialkyl ammonium salts, alkyl pyridinium salts, triethanolamine oleate, benzethonium chloride, sodium lauryl sulfonate, ammonium lauryl sulfonate, dodecyl benzene sulfonate, sodium lauryl ether sulfate, diethanolamine lauryl sulfate, ammonium salts of sulfated alcohol ethoxylates, sodium cocoyl isethionate, sodium N-methyl-N-oleoyl taurate, sodium N-methyl-N-cocoyl taurate, triethanolamine lauryl sulfate, disodium monooleamide PEG-2 sulfosuccinate, petroleum sulfonates sodium salt, alkyl napthalene sodium sulfonates, sodium lauroyl sarcosinate, or sodium alkyl sulfosuccinate, alkyl beta aminopropionates, 2-alkylimidazoline quaternary ammonium salts, ricinoleamidopropyl betaine, cocamidopropyl betaine, stearyl betaine, stearyl amphocarboxy glycinate, sodium lauraminopropionate, cocoamidopropyl hydroxy sultaine, disodium laurylimino dipropionate, tallowiminodipropionate, cocoampho-carboxy glycinate, cocoimidazoline carboxylate, lauric imidazoline monocarboxylate, lauric imidazoline dicarboxylate, lauric myristic betaine, cocoamidosulfobetaine, alkylamidophospho betaine, lecithins and hydrogenated lecithins; lysolecithins and hydrogenated lysolecithins; phospholipids and derivatives thereof; and lysophospholipids and derivatives thereof.

3. The pharmaceutical composition according to claim 2, wherein the surfactant is polyethylene glycol-polypropylene glycol copolymer.

4. The pharmaceutical composition according to claim 1, wherein the one or more pH modifying agents is a combination of acid and alkali other than halogenide.

5. The pharmaceutical composition according to claim 1, wherein the one or more other pharmaceutically acceptable excipient(s) is/are selected from preservatives, isotonicity agents and diluents.

6. The pharmaceutical composition according to claim 5, wherein the preservatives are selected from the group consisting of benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, m-cresol and combinations thereof.

7. The pharmaceutical composition according to claim 5, wherein the isotonicity agents are selected from the group consisting of glycerin, sodium chloride, dextrose, lactose and combinations thereof.

8. The pharmaceutical composition according to claim 1, wherein the pharmaceutical composition has a pH of 2-8.

9. A pharmaceutical composition comprising Gly (A21), Arg (B31), Arg (B32)-human insulin, a solubility-enhancing agent, one or more pH modifying agent(s), and optionally one or more other pharmaceutically acceptable excipient(s), wherein the solubility-enhancing agent is selected from the group consisting of urea and glycine, and the glycine, when present, is present at about 0.1 mg/ml to about 2.5 mg/ml.

10. The pharmaceutical composition of claim 9, wherein the pharmaceutical composition further comprises a surfactant other than a polyhydric alcohol.

11. The pharmaceutical composition of claim 9, wherein the pharmaceutical composition has a pH of 3.9 to 4.2.

12. The pharmaceutical composition according to claim 9, wherein the one or more other pharmaceutically acceptable excipients is/are selected from preservatives, isotonicity agents and diluents.

13. A process for preparing the stable aqueous pharmaceutical composition according to claim 1 comprising:
   a) preparing a solution comprising said solubility-enhancing agent and, optionally, one or more other pharmaceutically acceptable excipient(s),
   b) preparing a solution of insulin glargine and adding one or more pH modifying agent(s) to the solution, and
   c) mixing the solutions of steps a) and b) to produce the pharmaceutical composition according to claim 1.

14. A process for preparing the pharmaceutical composition according to claim 9 comprising:
   a) preparing a solution comprising one or more pH modifying agent(s);
   b) dissolving Gly(A21), Arg(B31), Arg(B32)-human insulin in acidic water to produce a solution;
   c) preparing a solution comprising said solubility-enhancing agent and, optionally, one or more other pharmaceutically acceptable excipient(s),
   d) mixing the solution of step (a) and with the solution of step (b); and
   e) adding the solution of step (c) to the solution of step (d) to produce the pharmaceutical composition according to claim 9.

15. A method for treating diabetes comprising administering to a subject in need thereof a pharmaceutical composition according to claim 1 or 9.

* * * * *